United States Patent [19]

Morishima et al.

[11] Patent Number: 5,316,758

[45] Date of Patent: May 31, 1994

[54] ORAL COMPOSITION

[75] Inventors: Seiji Morishima, Odawara; Yoji Yamazaki, Hiratsuka, both of Japan

[73] Assignee: Lion Corporation, Tokyo, Japan

[21] Appl. No.: 971,586

[22] Filed: Nov. 5, 1992

[30] Foreign Application Priority Data

Nov. 6, 1991 [JP] Japan .................. 3-318535

[51] Int. Cl.$^5$ .......................... A61K 7/16; A61K 7/22
[52] U.S. Cl. ...................................... 424/54; 424/49
[58] Field of Search ...................... 424/49-58

[56] References Cited

U.S. PATENT DOCUMENTS

| | | | |
|---|---|---|---|
| 3,804,946 | 4/1974 | Harrison et al. | 424/54 |
| 3,925,227 | 12/1975 | Corey et al. | 252/106 |
| 4,145,436 | 3/1979 | Michaels | 424/273 |
| 4,363,795 | 12/1982 | Wahlstam | 424/54 |
| 4,420,484 | 12/1983 | Gorman et al. | 424/326 |
| 4,762,642 | 8/1988 | Joshi et al. | 252/368 |
| 4,839,158 | 6/1989 | Michaels | 424/54 |
| 4,919,846 | 4/1990 | Nakama et al. | 252/542 |
| 5,098,608 | 3/1992 | Miyazawa et al. | 252/546 |
| 5,190,747 | 3/1993 | Sekiguchi et al. | 424/56 |
| 5,208,009 | 5/1993 | Gaffar et al. | 424/49 |

Primary Examiner—Shep K. Rose
Attorney, Agent, or Firm—Birch, Stewart Kolasch & Birch

[57] ABSTRACT

An oral composition comprises a nonionic antimicrobial or germicidal agent and at least one amphoteric surface active agent selected from the group consisting of compounds of the following general formulae (1) and (2):

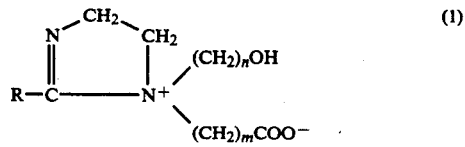

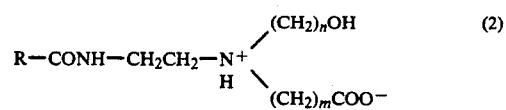

wherein R represents an alkyl group having 1 to 18 carbon atoms, and n and m are independently an integer of from 1 to 10. The composition preferably further comprises an alkyl sulfate.

15 Claims, No Drawings

ORAL COMPOSITION

BACKGROUND OF THE INVENTION

1. Industrial Field

The present invention relates to an oral composition in which a nonionic antimicrobial or germicidal agent is formulated and more particularly, to an oral composition which exhibits excellent dental plaque-inhibiting and gingivitis-preventive effects by permitting the nonionic antimicrobial or germicidal agent to be stayed in the mouth over a long time.

2. Prior Art

It is known to formulate,, in oral compositions such as dentifrice, cationic germicidal effective ingredients such as chlorhexidine, cetylpyridinium chloride and the like so that formation of dental plaque is inhibited. These cationic germicides are disadvantageous in that they suffer considerable deactivation when used in the presence of surface active agents which are commonly used as a foaming agent in oral compositions. Thus, their efficacy cannot be shown satisfactorily.

On the other hand, nonionic antimicrobial or germicidal agents suffer a less degree of the deactivation with the surface active agents and show their activity to an extent in the presence of the surface active agents. Accordingly, attention has been recently paid to these agents as an effective ingredient of oral compositions. Among known nonionic antimicrobial or germicidal agents, triclosan (2,4,4'-trichloro-2'-hydroxydiphenyl ether) which has a very intense germicidal activity and is innoxious to human body has attracted attention because of the capability of inhibiting plaque from being formed by its intense germicidal action. In fact, there has been proposed incorporation, in oral compositions comprising triclosan, of zinc salts (Japanese Laid-open Patent Application Nos. 60-239409 and 60-239410), copper compounds (Japanese Laid-open Patent Application No. 62-89614), polyethylene glycol (Japanese Laid-open Patent Application No. 62-126116), phenolic compounds (Japanese Laid- open Patent Application No. 2-11511), and water-soluble calcium salts (Japanese Laid-open Patent Application No. 3-5416).

However, nonionic antimicrobial or germicidal agents typical of which is triclosan are very unlikely to reside in the mouth. Accordingly, known nonionic antimicrobial or germicidal agent-containing oral compositions do not show their plaque inhibiting effect satisfactorily. Hence, there is a demand for improving the above deficiency.

SUMMARY OF THE INVENTION

An object of the present invention is to provide an oral composition containing a non-ionic antimicrobial or germicidal agent which can be stayed in the mouth over a long term to exert its effect, thereby preventing the formation of dental plaque and the occurrence of gingivitis.

We made intensive studies in order to solve the above problem and, as a result, found that when at least one amphoteric surface active agent selected from the group consisting of compounds of the following general formulae (1) and (2) are formulated in an oral composition which comprises a nonionic antimicrobial or germicidal agent such as triclosan, the residence of the nonionic antimicrobial or germicidal agent in the mouth can be prolonged. More particularly, since the nonionic anti-microbial or germicidal agent can be stayed in the mouth over a long term, the plaque formation-inhibiting and gingivitis-preventive effects are significantly exerted. In addition, when an alkyl sulfate is further added, the effects are synergistically enhanced. The invention is accomplished based on the above finding.

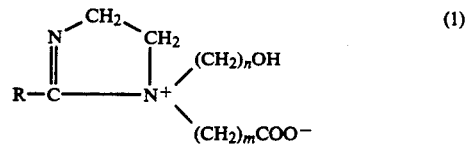

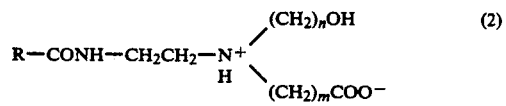

wherein R represents an alkyl group having 1 to 18 carbon atoms, and n and m are independently an integer of from 1 to 10.

Therefore, according to the present invention, there is provided an oral composition comprising a nonionic antimicrobial or germicidal agent and at least one amphoteric surface active agent selected from the group consisting of the compounds represented by the above formulae (1) and (2).

DETAILED DESCRIPTION OF THE INVENTION

The oral composition of the present invention can be used in the form of dentifrices such as toothpastes, toothpowders and liquid dentifrices, mouthwashes, gingiva-massage creams, liquid or paste regional ointments, troches, chewing gums and the like. The composition comprises, in combination, a nonionic antimicrobial or germicidal agent and a specific type of amphoteric surface active agent.

In the practice of the invention, the nonionic antimicrobial or germicidal agents include, for example, halogenated diphenyl ether compounds such as triclosan, halogenated carbanilides such as trichlorocarbanilide, phenolic compounds such as thymol, biozole and the like, and mixtures of one or more of these compounds. Among them, triclosan (2,4,4'-trichloro-2'-hydroxydiphenyl ether) is preferred.

The amount of the nonionic antimicrobial or germicidal agent is not critical and is generally in the range of 0.001 to 1.0% by weight, preferably 0.01 to 0.5% by weight of the total weight of the oral composition.

The amphoteric surface active agent used is at least one member selected from compounds of the following general formulae (1) and (2).

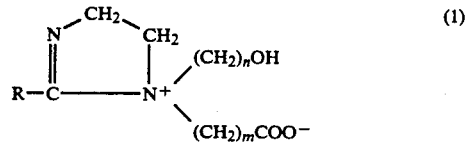

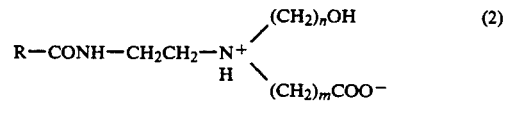

In the above formulae (1) and (2), R is an alkyl group having from 1 to 18 carbon atoms, preferably from 6 to 14 carbon atoms, and n and m are independently an integer of 1 to 10, preferably 1 to 4.

Specific examples of the amphoteric surface active agent include 2-undecyl-N-carboxymethyl-N-hydroxyethylimidazolinium betaine, 2-undecyl-N-carboxyethyl-N-hydroxyethylimidazolinium betaine, coconut oil alkyl-N-carboxymethyl-N-hydroxyethylimidazolinium betaine and the like.

The amount of the amphoteric surface active agent is in the range of 0.01 to 10% by weight, preferably 0.1 to 5% by weight of the total weight of the composition. If the amount is less than 0.01% by weight, the residence of the nonionic antimicrobial or germicidal agent such as triclosan in the mouth may not be realized satisfactorily. Over 10% by weight, the feel of the composition may be impeded.

Preferably, an alkyl sulfate is added to the composition of the present invention. The alkyl sulfate is favorably one which has an alkyl group having 8 to 18 carbon atoms, preferably 10 to 14 carbon atoms. Specific examples include sodium lauryl sulfate, sodium myristyl sulfate and the like.

The amount of the alkyl sulfate is in the range of 0.01 to 10% by weight, preferably 0.1 to 5% by weight of the total weight of the composition. If the amount is less than 0.01% by weight, the plaque-inhibiting effect of the resultant composition may not become satisfactory. When the amount exceeds 10% by weight, the feel in use may be lowered.

Depending on the purpose and the type of composition, the oral composition of the invention may further comprise, aside from the above-stated ingredients, abrasives, binders, humectants, flavors and other effective ingredients in amounts not impeding the effect of the invention.

Examples of the abrasive include calcium hydrogen phosphate dihydrate, calcium carbonate, calcium pyrophosphate, calcium sulfate, insoluble sodium metaphosphate, silicic anhydride, hydrous silicic acid, aluminosilicate, alumina, aluminum hydroxide, magnesium tertiary phosphate, magnesium carbonate, and synthetic resins, alone or in admixture of two or more (generally in amounts of 10 to 90% by weight based on the total weight of the composition, particularly 20 to 60% by weight in the case of toothpaste). Examples of the humectant include sorbitol, glycerin, propylene glycol, 1,3-tutylene glycol, polyethylene glycol, xylitol, maltitol, and lactitol, alone or in admixture of two or more (generally in amounts of 5 to 85% by weight based on the total weight of the composition). Examples of the binder include sodium carboxymethyl cellulose, carrageenan, sodium alginate, polyacrylic acid and salts thereof, gums, polyvinyl alcohol, and hydroxyethyl cellulose alone or in admixture of two or more (generally in amounts of 0.3 to 5% by weight based on the total weight of the composition).

Also included are sweeteners such as saccharin sodium, stevioside, neohesperidyl dihydrochalcone, taumatin, glycyrrhizin, perillartine, etc.; preservatives such as p-hydroxybenzoates, sodium benzoate, etc.; and other components. When p-hydroxybenzoates are used as preservatives, their amount should preferably be 0.2% by weight or less because more than 0.3% of p-hydroxybenzoates provides a stimulating taste, resulting in oral compositions of less pleasant feel.

Other forms of oral compositions may be prepared in a conventional manner using selected components for a particular form of composition.

The thus obtained composition is received in suitable containers such as aluminum tubes, laminate tubes in which aluminum foil is platic laminated on either surface, plastic tubes, bottles, aerosol containers, and the like before it is ready for use.

The oral composition of the invention exhibits high plaque formation-inhibiting and gingivitis-preventive effects since nonionic antimicrobial or germicidal agents can be stayed in the mouth over a long time.

EXAMPLES

The invention is more particularly described by way of examples, which should not be construed as limiting the invention. In examples., "%", is "% by weight".

EXAMPLE 1

In order to check the adsorption or residence of triclosan used as a nonionic germicide on the teeth, the following test was conducted.

10 mg of hydroxyapatite (made by BDH Co., Ltd.) was washed with a phosphate buffer solution (10 mM: pH=7.2), followed by immersion in saliva for 1 hour to coat the hydroxyapatite surfaces with a salivary component (pellicle). The saliva-coated hydroxyapatite was washed with the phosphate buffer solution, followed by gentle agitation in 100 µl of a composition having the following formulation for 30 minutes. Thereafter, the triclosan adsorbed on the hydroxyapatite was washed with the phosphate buffer solution and eluted with ethanol, followed by quantitative determination by high performance liquid chromatography (HPLC) under the following conditions. The results are shown in Table 1.

| Test composition | |
| --- | --- |
| | by weight |
| Propylene glycol | 4.0% |
| D-Sorbitol | 20.0 |
| Triclosan | 0.05 |
| Test chemicals indicated in Table 1 | 0.5 |
| Purified water | balance |
| Total | 100.0% |
| Quantitative determination conditions of HPLC | |
| Column: | TSK-gel ODS-80TM (Toso Co., Ltd.) (4.65 in diameter × 250 mm in length) |
| Elute: | methanol:water:phosphoric acid = 80:20:0.1 |
| Detection: | UV light 280 nm |

TABLE 1

| No. | Tested chemicals | Adsorption of triclosan on saliva-coated hydroxyapatite |
| --- | --- | --- |
| | distilled water | X |
| 1 | sodium lauryl sulfate | X |
| 2 | sodium $C_{12}$N-methyltaurine | X |
| 3 | $C_{12}$ succinic acid monoglyceride ester | △ |
| 4 | disodium lauryl succinate | △ |
| 5 | 2-undecyl-N-carboxymethyl-N-hydroxyethylimidazolinium betaine | ○ |
| 6 | lauryldimethylaminoacetic acid betaine | X |
| 7 | 2-undecyl-N-carboxymethyl-N-hydroxyethylimidazolinium betaine + 1% sodium lauryl sulfate | ⊙ |
| 8 | 2-undecyl-N-carboxymethyl-N-hydroxyethylimidazolinium betaine + | ○ |

TABLE 1-continued

| No. | Tested chemicals | Adsorption of triclosan on saliva-coated hydroxyapatite |
|---|---|---|
| | 1% $C_{12}$N-methyl taurine | |

Adsorption:
X: <10μg/HA
△: 10–20 μg/HA
○: 20–40 μg/HA
◉: >40 μg/HA

From the results of Table 1, it will be seen that the combination of triclosan and the imidazolinium betaine (Test No. 5) is better than the cases of the other tested compositions using other surface active agents with respect to the adsorption of the triclosan on the hydroxyapatite powder. Moreover, when sodium lauryl sulfate is further added in combination (Test No. 7), an synergistic increase in the adsorption of the triclosan on the hydroxy apatite is recognized.

EXAMPLE 2

In order to check whether or not the triclosan adsorbed and resided on the teeth acts to inhibit plaque from be formed, the following test was conducted.

150 mg of hydroxyapatite (Mitsui-Toatsu Chemical Co., Ltd.) was tableted by the use of an tablet press for IR spectroscopy to obtain an hydroxyapatite disk having a diameter of 10 mm, followed by sintering at 1300° C. for 1 hour. The test sample was immersed in saliva for 2 hours (37° C.) to coat the sample surface with a salivary component (pellicle). The saliva-coated sample was washed with the phosphate buffer solution and treated with a test solution for 30 minutes in the same manner as in Example 1. After sufficient washing with the phosphate buffer solution, the hydroxyapatite sample was immersed in 2.7 ml of a THB liquid medium (DIFCO Co., Ltd.), to which 0.3 ml of Actinomyces viscosus T14V liquid was added. After anaerobic cultivation at 37° C. for 24 hours, the hydroxyapatite sample was removed and washed with the phosphate buffer solution, followed by ultrasonic dispersion of plaque deposit and measurement of its turbidity at 550 nm to determine a degree of the plaque deposit. The results are shown in Table 2.

TABLE 2

| No. | Tested chemicals | Plaque deposit inhibition of trichlosan |
|---|---|---|
| 1 | distilled water (triclosan 0%): control | — |
| 2 | distilled water (triclosan 0.05%) | X |
| 3 | sodium lauryl sulfate | X |
| 4 | 2-undecyl-N-carboxymethyl-N-hydroxyethylimidazolinium betaine | ○ |
| 5 | 2-undecyl-N-carboxymethyl-N-hydroxyethylimidazolinium betaine + 1% sodium lauryl sulfate | ◉ |

Plaque deposit inhibition rate relative to the control:
X: less than 20%
○: 20–50%
◉: not less than 50%

From the results of Table 2, it will be seen that the combination of triclosan and the imidazolinium betaine is effective in inhibiting formation of plaque on the saliva-coated hydroxyapatite sample surfaces. This effect is synergistically enhanced when the alkyl sulfate is further added.

EXAMPLE 3

| Toothpaste | |
|---|---|
| Aluminum hydroxide | 45.0% |
| Gelling silica | 2.0 |
| Sorbitol | 25.0 |
| Sodium carboxymethyl cellulose | 1.0 |
| Sucrose monopalmitate | 1.0 |
| Sodium lauryl sulfate | 1.5 |
| Sodium saccharin | 0.2 |
| Ethanol | 0.1 |
| Sodium benzoate | 0.1 |
| Triclosan | 0.3 |
| 2-undecyl-N-carboxymethyl-N-hydroxyethyl-imidazolinium betaine | 0.5 |
| Flavor | 1.0 |
| Water | Balance |
| Total | 100.0% |

EXAMPLE 4

| Toothpaste | |
|---|---|
| Precipitated silica | 25.0% |
| Sorbitol | 25.0 |
| Glycerin | 25.0 |
| Polyvinyl pyrrolidone | 1.0 |
| Sodim polyacrylate | 1.0 |
| Lauryl polyglycerin ester | 1.0 |
| Polyoxyethylene (60 mol) sorbitan monolaurate | 0.5 |
| Sodium saccharin | 0.2 |
| Ethyl p-oxybenzoate | 0.1 |
| Chlorhexidine (hydrochloric acid salt) | 0.1 |
| Triclosan | 0.2 |
| Biozole | 0.1 |
| 2-aklyl-N-carboxymethyl-N-hydroxyethylimidazolinium betaine | 0.8 |
| Flavor | 1.0 |
| Water | Balance |
| Total | 100.0% |

EXAMPLE 5

| Toothpaste | |
|---|---|
| Calcium hydrogen phosphate dihydrate | 20.0% |
| Calcium hydrogen phosphate anhydride | 20.0 |
| Gelling silica | 2.0 |
| Sorbitol | 20.0 |
| Propylene glycol | 2.5 |
| Sodium carboxymethyl cellulose | 1.0 |
| Lauryl diethanol amide | 1.0 |
| Sodium lauryl sulfate | 1.0 |
| Sodium lauroyl sarcosinate | 0.3 |
| Sodium saccharin | 0.1 |
| Ethyl p-oxybenzoate | 0.1 |
| Triclosan | 0.2 |
| 2-aklyl-N-carboxyethyl-N-hydroxyethylimidazolinium betaine | 0.5 |
| Flavor | 0.8 |
| Water | Balance |
| Total | 100.0% |

EXAMPLE 6

| Oral paste | |
|---|---|
| Cetanol | 10.0% |
| Squalane | 20.0 |
| Gelling silica | 5.0 |
| Polyoxyethylene (40 mol) hydrogenated castor oil | 0.1 |
| Sorbitan monooleate | 1.0 |
| Sodium lauryl sulfate | 0.2 |
| Glycyrrhetinic acid | 0.1 |
| Sodium sacharin | 0.6 |
| Triclosan | 0.3 |
| 2-undecyl-N-carboxymethyl-N-hydroxyethylimidazolinium betaine | 0.5 |
| Flavor | 0.6 |
| Water | Balance |
| Total | 100.0% |

EXAMPLE 7

| Oral paste | |
|---|---|
| Liquid paraffin | 15.0% |
| Cetanol | 10.0 |
| Glycerin | 20.0 |
| Sorbitan monooleate | 0.6 |
| Polyoxyethylene (40 mol) sorbitan monostearate | 5.0 |
| Sodium saccharin | 0.3 |
| Benzetonium chloride | 0.1 |
| Triclosan | 0.2 |
| 2-alkyl-N-carboxymethyl-N-hydroxyethylimidazolinium betaine | 0.7 |
| Flavor | 0.5 |
| Water | Balance |
| Total | 100.0% |

EXAMPLE 8

| Mouthwash | |
|---|---|
| Sorbitol | 10.0% |
| Ethanol | 5.0 |
| Polyoxyethylene (60 mol) hydrogenated castor oil | 0.1 |
| Sucrose monopalmitate | 0.2 |
| Sodium lauryl sulfate | 0.05 |
| Sodium saccharin | 0.2 |
| Triclosan | 0.05 |
| 2-undecyl-N-carboxymethyl-N-hydroxyethylimidazolinium betaine | 0.7 |
| Flavor | 0.6 |
| Water | Balance |
| Total | 100.0% |

EXAMPLE 9

| Troche | |
|---|---|
| Lactose | 97.0% |
| Polyoxyethylene (60 mol) monostearate | 0.2 |
| Sodium lauryl sulfate | 0.05 |
| Chlorhexidine (gluconic acid salt) | 0.02 |
| Stevia extract | 0.2 |
| Triclosan | 0.2 |
| 2-alkyl-N-carboxyethyl-N-hydroxymethylimidazolinium betaine | 0.5 |
| Flavor | 0.02 |
| Hydroxyethyl cellulose | Balance |
| Total | 100.0% |

We claim:

1. An oral composition comprising triclosan and an amphoteric surface active agent having the following general formula (1):

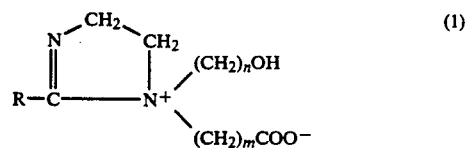

wherein R represents an alkyl group having 1 to 18 carbon atoms, and n and m are independently an integer of from 1 to 10, wherein triclosan is present in an amount from 0.001 to 1.0% by weight and said amphoteric surface active agent is present in an amount of from 0.01 to 10% by weight of the total weight of the composition.

2. The oral composition according to claim 1, wherein the amphoteric surface active agent is selected from the group consisting of 2-undecyl-N-carboxymethyl-N-hydroxyethylimidazolinium betaine, 2-undecyl-N-carboxyethyl-N-hydroxyethylimidazolinium betaine and coconut oil alkyl-N-carboxy-methyl-N-hydroxyethylimidazolinium betaine.

3. The oral composition according to claim 1 which further comprises an alkylsulfate having 8 to 18 carbon atoms in the alkyl group, wherein said alkylsulfate is present in an amount from 0.01 to 10% by weight of the total weight of the composition.

4. The composition according to claim 3, wherein said alkylsulfate has 10 to 14 carbon atoms in the alkyl group.

5. The composition according to claim 3, wherein said alkylsulfate is sodium lauryl sulfate or sodium myristyl sulfate.

6. The composition according to claim 3, wherein said alkylsulfate is present in an amount from 0.1 to 5% by weight.

7. The composition according to claim 5, wherein said alkylsulfate is present in an amount from 0.1 to 5% by weight.

8. The composition according to claim 1, wherein said triclosan is present in an amount from 0.01 to 0.5% by weight.

9. The composition according to claim 1, wherein said amphoteric surface active agent is present in an amount from 0.1 to 5% by weight.

10. The composition according to claim 1, wherein R is an alkyl group having from 6 to 14 carbon atoms.

11. The composition according to claim 1, wherein n and m are independently an integer of 1 to 4.

12. The composition according to claim 1, which further comprises 5 to 85% by weight, based on the total weight of the composition, of a humectant.

13. The composition according to claim 12, wherein said humectant is selected from the group consisting of sorbitol, glycerin, propylene glycol, 1,3-tutylene glycol, polyethylene glycol, xylitol, maltitol, lactitol, and combinations thereof.

14. The composition according to claim 3, which further comprises 5 to 85% by weight, based on the total weight of the composition, of a humectant.

15. The composition according to claim 13, wherein said humectant is selected from the group consisting of sorbitol, glycerin, propylene glycol, 1,3-tutylene glycol, polyethylene glycol, xylitol, maltitol, lactitol, and combinations thereof.

* * * * *